United States Patent

Ceccarelli et al.

[11] Patent Number: 6,124,287
[45] Date of Patent: Sep. 26, 2000

[54] IMIDAZO[1,2-A]QUINOXALIN-4-AMINES ACTIVE AS ADENOSINE ANTAGONISTS, PROCESS FOR THEIR PREPARATION AND PHARMACEUTICAL COMPOSITIONS THEREOF

[75] Inventors: Stefano Ceccarelli, Castelmassimo Di Veroli; Sergio Zanarella, Mentana; Maria Altobelli, Frosinone; Alessandra D'Alessandro, Sora, all of Italy

[73] Assignee: Biomedica Foscama Industria Chimicofarmaceutica S.p.A., Ferentino, Italy

[21] Appl. No.: 09/068,515
[22] PCT Filed: Nov. 22, 1996
[86] PCT No.: PCT/IB96/01291
§ 371 Date: May 12, 1998
§ 102(e) Date: May 12, 1998
[87] PCT Pub. No.: WO97/19079
PCT Pub. Date: May 29, 1997

[30] Foreign Application Priority Data

Nov. 24, 1995 [IT] Italy .................. MI95A2446

[51] Int. Cl.⁷ .................. A61K 31/4985; C07D 487/04
[52] U.S. Cl. .................. 514/233.2; 514/250; 544/115; 544/346
[58] Field of Search .................. 544/346, 115; 514/250, 233.2

[56] References Cited

U.S. PATENT DOCUMENTS 4,229,452  10/1980  Warner et al. .................. 544/346
4,780,464  10/1988  Trivedi et al. .................. 514/250
5,182,386   1/1993  Albaugh et al. .................. 540/350

FOREIGN PATENT DOCUMENTS

94/22865  10/1994  WIPO.

OTHER PUBLICATIONS

Simonov et al, Chemical Abstracts, vol. 77, No. 88433, 1972.
van Galen et al., J.Med. Chem., vol. 34, p.1202–1206, 1991.

*Primary Examiner*—Emily Bernhardt
*Attorney, Agent, or Firm*—Young & Thompson

[57] ABSTRACT

Imidazo[1,2-a]quinoxalin-4-amines derivatives of formula (I)

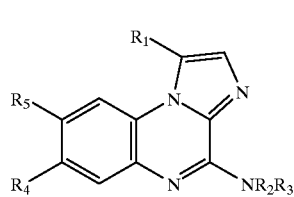

are described, and salt thereof active as adenosine antagonists and a process for their preparation and pharmaceutical compositions containing them as therapeutically active compounds for psychiatric and neurological disorders of the central nervous system.

4 Claims, No Drawings

IMIDAZO[1,2-A]QUINOXALIN-4-AMINES ACTIVE AS ADENOSINE ANTAGONISTS, PROCESS FOR THEIR PREPARATION AND PHARMACEUTICAL COMPOSITIONS THEREOF

DESCRIPTION

The present invention relates to the imidazo[1,2-a] quinoxalin-4-amines and their salts, that are active as antagonists of the adenosine receptors; a process for their preparation as well as the pharmaceutical compositions containing them as active ingredients that are useful in the tharphy for the treatment of various psychiatric and neurological disorders of the central nervous system.

It is known that theophylline (1,3-dimethylxanthine) and caffeine (1,3,7-trimethylxanthine) are capable of antagonizing the effect of adenosine through interaction with its receptors, and that it is mainly to such a property that their central nervous system stimulant effects are to be ascribed. However the presence of pharmacologically relevant effects also at the heart, kidney and smooth muscle level has determined a serious limitation to the therapeutical use of these substances as agents for effectively treating the central nervous system diseases characterized by abnormalities in the neuronal transmission processes, such as, for example, depression and senile dementia. Moreover, their low affinity to the adenosine receptors implies that the therapeutically effective dosages are too close to those causing serious side effects at the central level too. A series of compounds having various non-xanthine structures have exhibited in a various amount, affinity to the adenosine receptors (see for example documents EP 515,107 A2 and *J. Med. Chem.* 1991, 34, 1202), but none of them has the structure of imidazo[1,2-a]quinoxalin-4-amines.

Several derivative of imidazo[1,2-a]quinoxalin-4-amines have been described in the literature: for example in U.S. Pat. No. 5,182,386 imidazoquinoxalines are disclosed that interact with the central receptors of GABA, whilst in WO 94/22865 analogous compounds (especially derivatives of 4,5-dihydro-4-oxoimidazo [1,2-a]quinoxaline-2-carboxylic acid) are described as antagonists of excitatory amino acids. In no case, however, an affinity of such substances to the adenosine receptors has been pointed out. U.S. Pat. No. 4,229,452 discloses N-cyclohexyl-, N-butyl-, N-propylimidazo[1,2-a]quinoxalin-4-amine Chemical Abstracts 1972, 77:88433s describes imidazo[1,2-a] quinoxalin-4-amine. Such compounds, along with the whole subclass of unsubstituted N-alkyl- and N-cycloalkyl imidazo [1,2-a]quinoxalin-4-amines have been excluded from claim 1.

U.S. Pat. No. 4,780,464 and J. Med. Chem. 1990, 33, 2240–2254 disclose [1,2,4]triazolo[4,3-a]quinoxalin-4-amines having activity as adenosine antagonists and antidepressants. Such compounds are different from those claimed in the present invention. In addition, they are not particularly potent as antidepressants, having minimum effective doses in the Porsolt's forced swim test not lower than 1 mg/kg orally, with a consequent risk of developing significant side effects.

With the present invention, it has surprisingly been discovered that a group of imidazo[1,2-a]quinoxalin- 4-amines are potent antagonists of the adenosine receptors that are active in vivo onto the central nervous system at much lower dosage as compared with the compounds that are presently in general use in theraphy.

The compounds of the invention might therefore exhibit a lower incidence of side effects, especially at the peripheral level.

The present invention relates therefore to a compound of the formula (I):

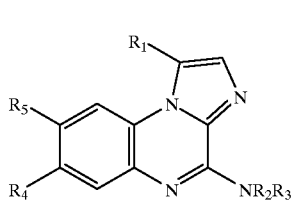

wherein $R_1$ is hydrogen or methyl;

$R_2$ is hydrogen, straight- or branched- chain $(C_1-C_6)$ alkyl;

$R_3$ is hydrogen, straight- or branched- chain $(C_1-C_8)$ alkyl that is possibly substituted with OH, $(C_3-C_8)$ cycloalkyl;

or $R_2$ and $R_3$ together form

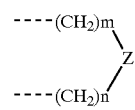

wherein Z is a direct bond, or O, $NR_6$, $R_6$ being a straight- or branched- chain $(C_1-C_6)$ alkyl;

m and n, same or different, are 1, 2 or 3;

$R_4$ and $R_5$ can be the same or different and are hydrogen or halogen chosen from Cl, F, Br; with the proviso that when $R_1$, $R_2$, $R_4$, $R_5$ are hydrogen, $R_3$ can not be hydrogen, straight- or branched-chain $(C_1-C_8)$ alkyl, $(C_3-C_8)$cycloalkyl;

and its pharmacologically acceptable salts;

In the present invention, there are preferred the compounds of formula (I) in which $R_1$ is hydrogen or methyl, $R_2$ is hydrogen, $R_3$ is hydrogen, straight- or branched- chain $(C_1-C_6)$alkyl, that is possibly substituted with OH, $(C_5-C_6)$ cycloalkyl, $R_4$ and $R_5$ can be the same or different and are hydrogen, chlorine or fluorine, with the proviso that when $R_1$, $R_2$, $R_4$, $R_5$ are hydrogen, $R_3$ can not be hydrogen, straight- or branched-chain $(C_1-C_8)$ alkyl, $(C_3-C_8)$cycloalkyl.

Especially preferred is the compound of formula (I) in which $R_1$ is methyl, $R_2$ is hydrogen, $R_3$ is cyclopentyl, $R_4$ and $R_5$ are both hydrogen, that is the compound 4-cyclopentylamino-1-methylimidazo[1,2-a]quinoxaline.

The salts of the compounds of formula (I) comprise the acid addition salts that can be prepared in situ during the final isolation and the purification or by means of a separate reaction of the free base with the suitable organic or inorganic acid chosen, for example, from hydrochloric, hydrobromic, phosphoric, methaphosphoric, nitric, sulphonic, tartaric, aceetic, citric, malic, lactic, fumaric, benzoic, glycolic, gluconic, succinic and p-toluene sulfonic acids.

An object of the present invention is also a process for the preparation of the compounds of the general formula (I). Said process comprises reacting the 2,3-dichloroquinoxaline of the formula (II)

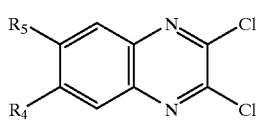

wherein R4 and R5 are as defined for the compound of formula (I), with amino acetaldehyde dimethyl acetal or with propargyl amine, thereby to obtain, respectively, the compounds of the formulae (III) and (IV)

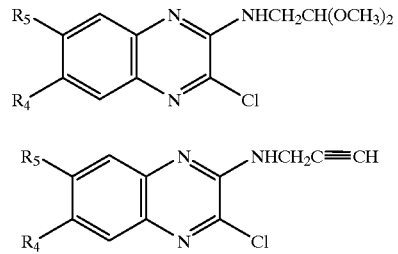

that are subsequently submitted to a cyclization reaction in an acidic medium, preferably at a temperature comprised between 50 and 120° C., to obtain the imidazo[1,2-a] quinoxalin-4(5H)-ones of the formula (V)

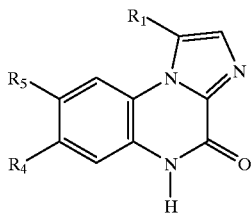

in which $R_1$ is hydrogen or methyl depending on whether the starting compound was compound (III) or compound (IV), respectively, $R_4$ and $R_5$ being as defined above.

The transformation of the compounds of formula (V) into the inventive compounds having the formula (I) can be carried out following two different synthetic sequences: in the first one, the chloride of the formula (VI)

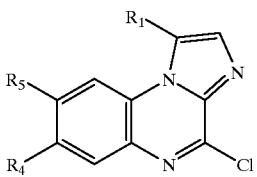

in which all the substituents are as already defined, said chloride being obtained by treatment of compound of formula (V) with $POCl_3$ or another chlorinating agent, is reacted with the suitable amine $HNR_2R_3$, in which $R_2$ is hydrogen, straight- or branched- chain $(C_1-C_8)$alkyl; $R_3$ is hydrogen, straight or branched chain $(C_1-C_8)$alkyl, possibly substituted with hydroxy, $(C_3-C_6)$cycloalkyl; or $R_2$ and $R_3$ together form

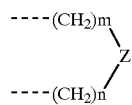

wherein Z is a direct bone, or O, $NR_6$, $R_6$ being a straight- or branched- chain $(C_1-C_6)$alkyl; m and n, same or different, are 1, 2 or 3.

As an alternative, the compound of formula (V) can be directly converted into the compounds of formula (I), by reacting it with a silylating agent, such as hexamethyl disilazane and the suitable amine $HNR_2R_3$ in which $R_2$ and $R_3$ are as defined in formula (I), at a temperature between 80 and 180° C., possibly in the presence of a catalyst, such as ammonium sulphate.

The preparation of the compounds of formula (I) in which $R_2$ and $R_3$ are both hydrogen, can also be carried out by reacting the chloride of formula (VI) with hydrazine to obtain a compound of formula (VII)

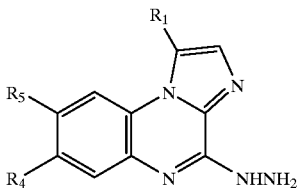

in which all the substituents are as defined above, followed by hydrogenation of this compound by conventional methods, such as, for example, hydrogen and palladium-on-carbon, or Raney nickel.

The preferred compound of the present invention can be prepared according to the general process described above through the formation of the compound of formula (V). Said compound is then converted to the preferred compounds of formula (I) by means of either synthetic sequence shown above. For example, the especially preferred compound of formula (I) of the present invention can be prepared by treating 2,3-dichloroquinoxaline (compound of formula (II) in which $R_4$ and $R_5$ are both hydrogen) with propargylamine to obtain the 2-propargylamino-3-chloroquinoxaline (compound of formula (IV) in which both $R_4$ and $R_5$ are hydrogen), followed by reacting this latter compound in an acidic medium, for example with the concentrated sulphuric acid, at a temperature of between 50 and 120° C., to give 1-methylimidazo[1,2-a]quinoxalin-4-(5H)-one (compound of formula (V) in which $R_1$ is methyl and $R_4$ and $R_5$ are both hydrogen). This compound can finally be converted to 4-cyclopentylamino-1-methylimidazo[1,2-a]quinoxaline through the formation of the intermediate 4-chloro-1-methylimidazo[1,2-a]quinoxaline (compound of formula (VI) in which $R_1$ is methyl and $R_4$ and $R_5$ are both hydrogen) by chlorination with one of known chlorinating agents at a temperature of between 50 and 150° C., followed by the reaction of the latter compound with cyclopentylamine, or alternatively, by reaction of 1-methylimidazo[1,2-a] quinoxalin-4(5H)-one with cyclopentylamine in hexamethyl disilazane or other silylating agent at a temperature of between 80 and 180° C., possibly in the presence of a catalyst, such as ammonium sulphate.

The preparation of the compounds of formula (II), when they are not commercially available, can be carried out with methods such as the one shown below. Specifically, phenylenediamine (VIII) is reacted with dialkyl oxalate to give the 2,3-dihydroxyquinoxaline (IX), wich is then subjected to a chlorinating reaction with one of the usual chlorinating agents, such as for example POCl₃, thereby obtaining the compounds (II)

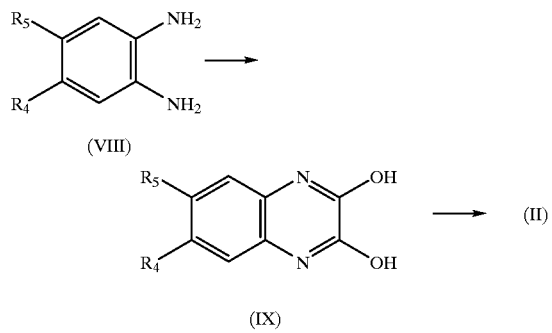

As shown hereinafter in Examples 28 to 30, the compounds of formula (I) of the present invention are antagonists of the adenosine receptors, are active on the central nervous system and can therefore be advantageously used as active ingredients for the preparation of medicaments that are useful in therapy for the treatment of various psychiatric disorders of the central nervous system, such as the depressive syndromes of various etiology and symptomatology and mood disorders in general, bulimia nervosa, sleep disorders, obsessive-compulsive disorders, phobias, panic attacks. Further indications are neurological diseases, such as pre-senile and senile dementia, the Alzheimer's disease, the multiinfarctual dementias, the encephalopathies of toxic or traumatic origin, the Parkinson disease, the post-neurological deficits, the respiratory depression, the neonatal cerebral damage.

Besides being employed as drugs acting on the central nervous system, the compounds of the present invention and their salts could be used for the treatment of diseases of the renal system, such as acute renal failure, or of diseases of the cardiovascular system.

For all the above-mentioned therapeutical uses, the compounds of the present invention can be administered by oral, transdermal or transmucosal route, parenterally or rectally in formulations containing them as the active ingredients at a therapeutically effective dosage with conventional, non-toxic pharmaceutical excipients. The term parenteral as used herein comprises subcutaneous, intravenous, intramuscolar and intracerebroventricular injections. If the compounds of the present invention are in the form of a pharmaceutical composition, as in a preferred embodiment of the invention, the precise formulation employed will obviously depend on the administration route chosen.

The pharmaceutical compositions that are suitable for the oral administration can be for example tablets, aqueous or oily suspensions, dispersible powders or granules, hard or soft capsules, syrups or elixirs. The compositions for the oral administration can contain one or more sweetening agents, colorants, flavouring and preserving agents that are suitable to make the pharmaceutical composition elegant and palatable.

The formulations for oral administration comprise tablet in which the active ingredient is admixed with non-toxic, pharmaceutically acceptable excipients. Said excipients can be inert diluents, such as calcium carbonate, sodium carbonate, lactose, calcium phosphate or sodium phosphate; granulating or disgregating agents, such as wheat starch or alginic acid; binding agents, such as starch or gelatines; lubricant agents, such as magnesium stearate, stearic acid or talc.

The tablets can be non-coated or coated with conventional techniques known to a person skilled in the art in order to delay disintegration and absorption in the gastrointestinal tract, in order to achieve a sustained release action.

The aqueous suspensions generally contain the active ingredients admixed with the suitable excipients. The excipients can be suspending agents, such as sodium carboxymethyl cellulose, methyl cellulose, hydroxypropyl methyl cellulose, sodium alginate, polyvinylpyrrolidone; dispersants and wetting agents. They can also contain one or more preservatives, such as ethyl and n-propyl p-hydroxybenzoate; one or more flavouring agent; one or more sweetening agents.

The oily suspensions can be formulated by suspending the active ingredient in a vegetable or mineral oil; they can contain sweetening agents and flavouring agents in order to make the preparation palatable.

The dispersible powders and granules that are suitable to the preparation of an aqueous suspension by adding water contain the active ingredient in admixture with the dispersing or wetting agent, a suspending agent and one or more preserving agents.

The pharmaceutical compositions of the present invention can also be in the form of a water/oil emulsion. The oily phase can consist of a vegetable or mineral oil. The emulsifying agents can be natural gums, such as acacia, or natural phosphatides, such as lecithins, or natural or synthetic fatty acid esters. The syrups and the elixirs can be formulated with sweetening agents, for example glycerol, sorbitol or sucrose.

The pharmaceutical compositions can be in the form of aqueous or oily, sterile injectable suspensions. The suspensions can be formulated with the known techniques by using dispersing or wetting agents and suspending agents that are known in the art. The sterile injectable preparations can be sterile injectable solutions or suspensions in a non-toxic solvent or diluent that is suitable for the parenteral use.

The compounds of the present invention can also be administered by the rectal route in the form of suppositories. These composition can be prepared by mixing the active ingredient with a suitable, non irritating excipient that is solid at room temperature but liquid at the rectal temperature, thereby melting in rectum to release the drug. The polyethylene glycols and the cocoa butter are suitable compounds for this purpose.

The therapeutically or prophylactically effective amounts of a compound of the present invention will depend on a number of factors including, for example, the age and weight of the patient, the severity of the specific disease requiring the treatment, the administration route. However, an effective amount of the compound of the present invention for the treatment of depressive syndromes and of senile dementia will generally be comprised in the range of 0.005–20 mg/kg of body weight per day, more frequently in the range of 0.05–2 mg/kg per day.

In order to better illustrate the present invention, the following examples are reported, that are in no way to be considered as limiting.

EXAMPLE 1

(a) A mixture of 5.0 g of 2,3-dichloroquinoxaline and 5.5 ml of aminoacetaldehyde dimethyl acetal in 75 ml of ethanol is refluxed for 4 h. After concentrating under vacuum, the resulting mixture is added with water and extracted with ethyl acetate. The organic extracts are then washed with saturated NaCl, dried and evaporated. The residue is finally chromatographed on $SiO_2$ (eluent: $CH_2Cl_2$), thereby obtaining 5.0 g of 2-chloro-3-(2,2-dimethoxyethylamino)quinoxaline (IR (KBr): 3347, 2936, 1580, 1523, 1129 $cm^{-1}$). 4.5 g of this product are then treated with 20 ml of 48% HBr and the mixture is refluxed for 4 h. After cooling down, the mixture is neutralized with aqueous NaOH and the resulting precipitate is filtered under vacuum and dried to obtain 3.2 g of imidazo[1,2-a]quinoxalin-4(5H)-one (m.p. >300° C.)

(b) A mixture of 0.47 g of imidazo[1,2-a]quinoxalin-4(5H)-one and 0.42 ml of N,N-dimethylaniline in 5.6 ml of phosphorous oxychloride is refluxed for 2 h. After evaporating under vacuum the resulting mixture, the residue is taken up in chloroform and repeatedly washed with water, then with saturated NaCl, then it is dried and evaporated thereby obtaining, after recrystallization from n-hexane/chloroform, 0.29 g of 4-chloroimidazo-[1,2-a]quinoxaline (IR (KBr): 1456, 755 $cm^{-1}$).

(c) A mixture of 0.25 g of 4-chloromidazo[1,2-α]quinoxaline and 0.5 ml of hydrazine hydrate in 1.5 ml of ethanol is refluxed for 2 h. After cooling the mixture, the resulting precipitate is filtered under vacuum, washed and dried, thereby obtaining 0.22 g of 4-hydrazinoimidazo[1,2-a]quinoxaline (IR (KBr): 3308, 3237, 1570 $cm^{-1}$).

(d) A mixture of 0.17 g of 4-hydrazinoimidazo[1,2-a]quinoxaline and 3.4 ml of Raney nickel in 20 ml of water is refluxed for 1.5 h. After cooling down, the mixture is filtered on Celite, followed by washing with methanolic chloroform. The filtrate is concentrated under vacuum and extracted with ethyl acetate. The organic extracts are then washed with saturated NaCl, dried and evaporated, thereby obtaining 0.17 g of imidazo[1,2-a]quinoxalin-4-amine. M.p. (DSC)=205.3° C. (onset); IR (KBr): 3301, 3143, 1653, 1525 $cm^{-1}$; $^1$-NMR ($CDCl_3$): δ8.0 (1H,s), 7.8÷7.45 (3H,m), 7.45÷7.2 (2H,m), 5.8 (2H,sb); UV (EtOH): $\lambda_{max}$=229, 295, 331 nm. Elementary analysis for $C_{10}H_3N_4$ (m.w. 184.20): calcd. C 65.21, H 4.38, N 30.42%; found C 65.48, H 4.71, N 30.10%;.

EXAMPLE 2

(a) A mixture of 10 g of 2,3-dichloroquinoxaline, 4.5 ml of propargylamine, 10.5 ml of triethylamine in 50 ml of ethanol is refluxed for 4 h. After evaporating under vacuum the resulting mixture, the residue is chromatographed on $SiO_2$ (eluent: $CH_2Cl_2$) thereby obtaining 7.0 g of 2-chloro-3-(propargylamino)quinoxaline (IR (KBr): 3441, 3282, 1518 $cm^{-1}$). This product is then added with 10 ml of concentrated sulphuric acid and the resulting mixture is stirred at 90° C. for 1 h. After cooling down and cautiously neutralizing with aqueous NaOH, the resulting precipitate is filtered under vacuum, washed, dried, decolorized and recrystallized from dimethylformamide, thereby obtaining 2.4 g of 1-methylimidazo[1,2-a]quinoxaline-4(5H)-one (m.p. >300° C.).

(b) The chlorination of 1-methylimidazo[1,2-a-]quinoxalin-4(5H)-one with $POCl_3$ is carried out according to a closely analogous procedure to that reported in example 1 (b), thereby obtaining 4-chloro-1-methylimidazo[1,2-a]quinoxaline (IR (KBr): 1486, 754 $cm^{-1}$).

(c) The reaction of 4-chloro-1-methylimidazo[1,2-a]quinoxaline with hydrazine hydrate is carried out according to a strictly analogous procedure to that followed in example 1 (c), thereby obtaining 4-hydrazino-1-methylimidazo[1,2-a]quinoxaline (IR (KBr): 3298, 3250, 1564 $cm^{-1}$).

(d) The hydrogenation of 4-hydrazino-1-methylimidazo[1,2-a]quinoxaline with Raney nickel is carried out according to a strictly analogous procedure to that followed in example 1 (d), thereby obtaining 1-methylimidazo[1,2-a]quinoxaline-4-amine. m.p. (DSC)=184.8° C. (onset); IR (KBr): 3379, 3295, 1640, 1516 $cm^{-1}$; $^1$H-NMR ($CDCl_3$): δ8.05 (1H,dd), 7.9÷7.2 (3H,m) 7.2 (1H,s), 5,7 (2H, sb), 2.85 (3H, s); UV (EtOH): $\lambda_{max}$=225, 270, 304, 329 nm. Elementary analysis for $C_{11}H_{10}H_4$ (m.w. 198.23): calcd. C 66.65, H 5.08, N 28.26%; found C 66.79, H 5.30, N 28.03%.

EXAMPLE 3

A mixture of 2,8 g of 4-chloroimidazo[1,2-a]quinoxaline (example 1) and 9.8 ml of diethylamine in 40 ml of ethanol is refluxed for 4 h. After evaporating the solvent, the residue is taken up in chloroform and washed with water and saturated NaCl, then dried and evaporated, thereby obtaining 2.2 g of raw product that is subsequently chromatographed on $SiO_2$ (eluent: $CH_2Cl_2$): after recrystallization from n-hexane there are obtained 1.3 g of 4- diethylaminoimidazo[1,2-a]quinoxaline. m.p. (DSC)=91.7° C. (onset); IR (KBr): 2976, 1518, 1425, $cm^{-1}$; $^1$H-NMR ($CDCl_3$): δ7.9 (1H,s), 7.7÷7.4 (3H,m), 7.35÷7.05 (2H,m), 4.15 (4H,q), 1.3 (6H,t); UV (EtOH): $\lambda_{max}$=231, 250, 293, 305, 332, 348 nm. Elementary analysis for $C_{14}H_{16}N_4$ (m.w. 240.31): calcd. C 69.97, H 6.71, N 23.31%; found C 69.99, H 6.80, N 23.13%.

EXAMPLE 4

By reaction of 4-chloroimidazo[1,2-a]quinoxaline (example 1) with isopropylamine according to a procedure that is similar to that followed in example 3 there is obtained 4-isopropylaminoimidazo[1,2-a]quinoxaline. m.p. (DSC)=102.7° C. (onset); IR (KBr): 3230, 2966, 1559 $cm^{-1}$; $^1$H-NMR (DMSO-$d_6$): δ8.55 (1H,s), 8.2÷7.95 (1H,m), 7.6÷7.4 (2H,m), 7.4÷7.2 (3H,m), 4.5 (1H,m), 1.25 (6H,d); UV (EtOH): $\lambda_{max}$=227, 244, 285, 297, 318, 332 nm. Elementary analysis for $C_{13}H_{14}N_4$ (m.w. 226.28): calcd. C 69.00, H 6.23, N 24.76%; found C 69.17, H 6.70, N 25.05%.

EXAMPLE 5

By reaction of 4-chloro-1-methylimidazo[1,2-a]quinoxaline (example 2) with 1-ethylpropylamine, according to a procedure that is similar to that followed in example 3 there is obtained 4-(1-ethylpropylamino)-1-methylimidazo[1,2-a] quinoxaline. m.p. (DSC)=75.9° C. (onset); IR (KBr): 3231, 2965, 1546 $cm^{-1}$; $^1$H-NMR ($CDCl_3$): δ8.0 (1H,dd), 7.7 (1H,dd), 7.4÷7.1 (3H,m), 5.9 (1H,d), 4.2 (1H,m), 2.85 (3H,s), 1.65 (4H,m), 0.95 (6H,t); UV (EtOH): $\lambda_{max}$=221, 241, 268, 298, 313 nm. Elementary analysis for $C_{14}H_{20}N_4$ (m.w. 268.36): calcd. C 71.61, H 7.51, N 20.83%; found C 71.12, H 7.53, N 20.79%.

EXAMPLE 6

By reaction of 4-chloroimidazo[1,2-a]quinoxaline (example 1) with ethanolamine according to a procedure that is similar to that followed in example 3 there is obtained 4-(2-hydroxyethylamino)imidazo[1,2-a]quinoxaline. m.p. (DSC)=150.8° C. (onset); IR (KBr): 3312, 1598, 1564 $cm^{-1}$; $^1$H-NMR ($CDCl_3/CD_3OD$): δ8.2 (1H,s), 8.1÷7.55 (2H,m), 7.55 (1H,s), 7.4÷7.2 (2H,m), 3.8 (4H,s); UV (EtOH): $\lambda_{max}$=227, 285, 297, 317, 330 nm. Elementary analysis for $C_{12}H_{12}N_4$ (m.w. 228.25): calcd. C 63.14, H 5.30, N 24.55%; found C 63.16, H 5.40, N 24.99%.

EXAMPLE 7

By reaction of 4-chloro-1-methylimidazo[1,2-a]quinoxaline (example 2) with ethanolamine according to a procedure that is similar to that followed in example 3 there is obtained 4-(2-hydroxyethylamino)-1-methyl imidazo[1,2-a]quinoxaline. m.p. (DSC)=173.4° C. (onset); IR (KBr): 3415, 3217, 1558 cm$^{-1}$; $^1$H-NMR (CDCl$_3$): δ8.0 (1H,dd), 7.7÷7.2 (3H,m), 7.2 (1H,m), 6.6 (1H,m), 5.3 (1H,sb), 3.85 (3H,m), 2.8 (3H,s); UV (EtOH): $\lambda_{max}$=225, 242, 271, 301, 314, 327 nm. Elementary analysis for C$_{13}$H$_{14}$N$_4$ (m.w. 242.28): calcd. C 64.45, H 5.82, N 23.12%; found C 64.29, H 5.91, N 23.13%.

EXAMPLE 8

By reaction of 4-chloroimidazo[1,2-a]quinoxaline (example 1) with cyclopentylamine according to a procedure that is similar to that followed in example 3 there is obtained 4-cyclopentylaminoimidazo[1,2-a] quinoxaline. m.p. (DSC)=114.3° C. (onset); IR (KBr): 3419, 2962, 1543 cm$^{-1}$; $^1$H-NMR (CDCl$_3$):δ7.9 (1H,s), 7.8÷7.0 (5H,m), 6.2 (1H,d), 4.7 (1H, m), 2.3÷2.05 (4H,m), 2.0÷1.3 (4H,m); UV (EtOH): δ$_{max}$=228, 244, 285, 297, 319, 333 nm.

EXAMPLE 9

A mixture of 3.5 g of 1-methylimidazo[1,2-a] quinoxalin-4(5H)-one (example 2), 13 ml of hexamethyl disilazane, 0.5 g of ammonium sulphate and 8.7 ml dicyclopentylamine is stirred at 120° C. in a Dean-Stark apparatus for 24 h. After concentrating the resulting mixture under vacuum, the residue is added with water and extracted with ethyl acetate. The organic extracts are then washed with water and saturated NaCl, dried and evaporated, thereby obtaining 1.5 g of a raw product that is subsequently chromatographed on SiO$_2$ (eluent: CH$_2$Cl$_2$/AcOEt 97:3). By recrystallizing from ethyl acetate, there is obtained 4-cyclopentylamino-1-methyl imidazo [1,2-a]quinoxaline. m.p. (DSC)=167.3° C. (onset); IR (KBr): 3294, 2948, 1544 cm$^{-1}$; $^1$H-NMR (CDCl$_3$): δ8.0 (1H,dd), 7.4÷7.05 (3H,m), 6.0 (1H,d), 4.6 (1H,m), 2.8 (3H,s), 2.3÷2.05 (4H,m), 2.0÷1.4 (4H,m); UV (EtOH): $\lambda_{max}$=225, 243, 272 301, 316, 329 nm. Elementary analysis for C$_{16}$H$_{16}$N$_4$ (m.w. 266.35): calcd. C 72.15, H 6.81, N 21.03%; found C 71.86, H 6.81, N 20.79%.

EXAMPLE 10

By reaction of 4-chloroimidazo[1,2-a]quinoxaline (example 1) with cyclohexylamine, according to a procedure that is similar to that followed in example 3, there is obtained 4-cyclohexylaminoimidazo[1,2-a]quinoxaline. m.p. (DSC)=94.0° C. (onset); IR (KBr): 3227, 2924, 1560 cm$^{-1}$; $^1$H-NMR (CDCl$_3$): δ7.85 (1H,d, J=2 Hz), 7.8÷7.4 (3H,m), 7.4÷7.1 (2H,m), 6.0 (1H,d), 4.2 (1H,m), 2.3÷1.95 (3H,m), 1.95÷0.9 (6H,m); UV (EtOH): $\lambda_{max}$=225, 242, 283, 294, 316, 330 nm. Elementary analysis for C$_{16}$H$_{18}$N$_4$ (m.w.266.35): calcd. C 72.15, H 6.81, N 21.03%; found C 72.25, H 7.04, N 21.19%.

EXAMPLE 11

By reaction of 1-methylimidazo[1,2-a]quinoxaline-4(5H)-one (example 2) with cyclohexylamine, according to a procedure that is similar to that followed in example 9, there is obtained 4-cyclohexylamino-1-methyl imidazo [1,2-a] quinoxaline. m.p. (DSC)=126.5° C. (onset); IR (KBr): 3345, 2938, 1546 cm$^{-1}$; $^1$H-NMR (CDCl$_3$): δ8.0 (1H,dd), 7.7 (1H,dd), 7.5÷7.1 (3H,m), 6.0 (1H,d), 4.2 (1H,m), 2.85 (3H,s), 2.3÷1.95 (4H,m), 1.95÷0.9 (6H,m); UV (EtOH): $\lambda_{max}$=225, 243, 272, 301, 316, 329 nm. Elementary analysis for C$_{17}$H$_{20}$N$_4$ (m.w.280.37): calcd. C 72.83, H 7.19, N 19.98%; found C 72.21, H 7.54, N 20.14%.

EXAMPLE 12

By reaction of 4-chloroimidazo[1,2-a]quinoxaline (example 1) with piperidine, according to a procedure that is similar to that followed in example 3, there is obtained 4-(1-piperidinyl)imidazo[1,2-a]quinoxaline. m.p. (DSC)=108.2° C.(onset); IR (KBr): 3107, 2935, 1517 cm$^{-1}$; $^1$H NMR (CDCl$_3$): δ7.9 (1H,d, J=2 Hz), 7.75÷7.4 (3H,m), 7.4÷7.1 (2H,m), 4.3 (4H,t), 1.9÷1.6 (6H,m), 7.75÷7.4 (3H,m), 7.4÷7.1 (2H,m), 4.3 (4H,t) 1.9÷1.6 (6H,m); UV (EtOH): $\lambda_{max}$=231, 249, 293, 305, 333 nm. Elementary analysis for C$_{15}$H$_{16}$N$_4$ (m.w.252.32): calcd. C 71.40, H 6.39, N 22.20%; found C 71.38, H 6.63, N 22.61%.

EXAMPLE 13

By reaction of 4-chloro-1-methylimidazo[1,2-a] quinoxaline (example 2) with piperidine, according to a procedure that is similar to that followed in example 3, there is obtained 1-methyl-4-piperidinylimidazo[1,2-a] quinoxaline. m.p. (DSC)=78.9° C. (onset); IR (KBr): 3018, 2927, 1502 cm$^{-1}$; $^1$H-NMR (CDCl$_3$): δ8.05 (1H,dd), 7.65 (1H,dd), 7.5÷7.0 (3H,m), 4.25 (4H,t), 2.85 (3H,s), 1.9÷1.6 (6H,m); UV (EtOH): $\lambda_{max}$=249, 281, 297, 310, 329 nm. Elementary analysis for C$_{14}$H$_{18}$N$_4$ (m.w.266.35): calcd. C 72.15, H 6.81, N 21.03%; found C 71.84, H 7.09, N 20.70%.

EXAMPLE 14

By reaction of 4-chloroimidazo[1,2-a]quinoxaline (example 1) with morpholine, according to a procedure that is similar to that followed in example 3, there is obtained 4-(4-morpholinyl)imidazo[1,2-a]quinoxaline. m.p. (DSC)=142.8° C. (onset); IR (KBr): 3016, 2962, 1517 cm$^{-1}$; $^1$H-NMR (CDCl$_3$): δ8.0 (1H,s), 7.8÷7.5 (3H,m), 7.5÷7.2 (2H,m), 4.4 (4H,t), 3.9 (4H,t); UV (EtOH): $\lambda_{max}$=230, 248, 292, 304, 330 nm. Elementary analysis for C$_{14}$H$_{13}$N$_4$O (m.w. 254.29): calcd. C 66.13, H 5.55, N 22.03%; found C 65.43, H 5.47, N 22.25%.

EXAMPLE 15

By reaction of 4-chloroimidazo[1,2-a]quinoxaline (example 1) with N-methylpiperazine, according to a procedure that is similar to that followed in example 3, there is obtained 4-(N'-methylpiperazinyl)imidazo[1,2-a] quinoxaline. m.p. (DSC)=305.6° C.(onset); IR (KBr): 2697, 1560, 1508 cm$^{-1}$; $^1$H-NMR (DMSO-d$_6$/CD$_3$OD): δ8.7 (1H,sb), 8.3÷8.0 (1H,m), 7.8÷7.35 (4H,m), 5.5 (4H,t), 3.7÷3.3 (4H, m), 2.8 (3H,s); UV (EtOH): $\lambda_{max}$=230, 291, 304, 320 nm. Elementary analysis for C$_{15}$H$_{17}$N$_5$.2HCl (m.w. 340.25): calcd. C 52.95, H 5.63, N 20.58%; found C 52.81, H 5.78, N 20.13%.

EXAMPLE 16

By reaction of 4-chloro-1-methylimidazo[1,2-a] quinoxaline (example 2) with N-methylpiperazine, according to a procedure that is similar to that followed in example 3, there is obtained 1-methyl-4(N'-methylpiperazinyl) imidazo[1,2-a]quinoxaline. m.p. (DSC)=108.0° C.(onset); IR (KBr): 2928, 1535, 1510 cm$^{-1}$; $^1$H-NMR (CDCl$_3$): δ8.1 (1H,dd), 7.7 (1H,dd), 7.4÷7.0 (3H,m), 4.35 (4H,t), 2.85 (3H,s), 2.6 (4H,t), 2.3 (3H,s); UV (EtOH): $\lambda_{max}$=228, 248, 279, 309, 325 nm. Elementary analysis for C$_{16}$H$_{19}$N$_5$ (m.w. 281.36): calcd. C 68.30, H 6.81, N 24.89%; found C 68.37, H 7.15, N 25.05%.

EXAMPLE 17

By reaction of 2,3,6-trichloroquinoxaline with aminoacetaldehyde dimethyl acetal, according to a procedure that is similar to that followed in example 1, there is obtained 8-chloroimidazo[1,2-a]quinoxaline-4(5H)-one (m.p. >300° C.). By reacting this product with 1-ethyl propylamine according to the method described in example 9, there is obtained 8-chloro-4-(1-ethylpropylamino)imidazo[1,2-a] quinoxaline. m.p. (DSC)=125.1° C.(onset); IR (KBr): 3406, 3105, 2964, 1532 cm$^{-1}$; $^1$H-NMR (CDCl$_3$/CD$_3$OD): δ8.4 (1H,s), 8.05 (1H,d, J=2 Hz), 7.8÷7.4 (3H,m), 3.85 (1H,m), 1.65 (4H,m), 0.95 (6H,t); UV (EtOH): $\lambda_{max}$=230, 245, 289, 301, 326 nm. Elementary analysis for C$_{15}$H$_{17}$ClN$_4$ (m.w. 288.78): calcd. C 62.39, H 5.93, N 19.40%; found C 62.17, H 6.02, N 19.46%.

EXAMPLE 18

By reaction of 8-chloroimidazo[1,2-a]quinoxaline-4(5H)-one (example 17) with POCl$_3$, following a procedure that is similar to that described in example 1, there is obtained 4,8-dichloroimidazo[1,2-a]quinoxaline that is subsequently reacted with cyclopentylamine according to the method described in example 3, thereby obtaining 4-cyclopentylamino-8-chloroimidazo[1,2-a]quinoxaline. m.p. (DSC)=140.1° C.(onset); IR (KBr): 3401, 2955, 1554 cm$^{-1}$; $^1$H-NMR (CDCl$_3$): δ7.8 (1H,d, J=2 Hz), 7.7÷7.2 (4H,m), 6.15 (1H,d), 4.6 (1H,m), 2.3÷2.05 (4H,m), 2.05÷1.3 (4H,m); UV (EtOH): $\lambda_{max}$=229, 245, 289, 301, 326, 340 nm. Elementary analysis for C$_{15}$H$_{15}$ClN$_4$ (m.w. 286.76): calcd. C 62.83, H 5.27, N 19.54%; found C 63.04, H 5.36, N 19.64%.

EXAMPLE 19

By reaction of 4,8-dichloroimidazo[1,2-a]quinoxaline (example 18) with cyclohexylamine, following a procedure that is similar to that described in example 3, there is obtained 4-(1-cyclohexylamino-8-chloroimidazo[1,2-a] quinoxaline. m.p. (DSC)=126.7° C.(onset); IR (KBr): 3413, 2926, 1555 cm$^{-1}$; $^1$H-NMR (CDCl$_3$): δ7.85 (1H,s), 7.7÷7.2 (4H,m), 6.1 (1H,d), 4.2 (1H,m), 2.3÷2.0 (4H,m), 2.0÷1.2 (6H,m); UV (EtOH): $\lambda_{max}$=229, 245, 289, 301, 326, 340 nm. Elementary analysis for C$_{16}$H$_{17}$ClN$_4$ (m.w. 300.79): calcd. C 63.89, H 5.70, N 18.63%; found C 64.07, H 5.79, N 18.80%.

EXAMPLE 20

By reaction of 2,3,6-trichloroquinoxaline with propargylamine, following a procedure that is similar to that described in example 2, there is obtained 8-chloro-1-methylimidazo[1,2-a]quinoxaline-4(5H)-one (m.p. >300° C.) and, subsequently, 4,8-dichloro-1-methylimidazo[1,2-a] quinoxaline. By reacting this product with cyclopentylamine according to the method described in example 3, there is obtained 4-cyclopentylamino-8chloro-1-methylimidazo[1,2-a]quinoxaline. m.p. (DSC)=130.5° C.(onset); IR (KBr): 3421, 2954, 1555 cm$^{-1}$; $^1$H-NMR (CDCl$_3$): δ7.95 (1H,d, J=2 Hz), 7.6 (1H,d, J=9 Hz), 7.35÷7.15 (2H,m), 6.1 (1H,d), 4.5 (1H,s), 2.8 (3H,s), 2.4÷2.05 (4H,m), 2.0÷1.3 (4H,m); UV (EtOH): $\lambda_{max}$=227, 251, 276, 305, 336 nm. Elementary analysis for C$_{16}$H$_{17}$ClN$_4$ (m.w. 300.79): calcd. C 63.89, H 5.70, N 18.63%; found C 63.79, H 5.79, N 18.58%.

EXAMPLE 21

By reaction of 2,4-dichloro-1-methylimidazo[1,2-a] quinoxaline (example 20) with cyclohexylamine, following a procedure that is similar to that described in example 3, there is obtained 4-cyclohexylamino-8-chloro-1-methylimidazo [1,2-a]quinoxaline. m.p. (DSC)=130.4° C.(onset); IR (KBr): 3410, 2927, 1551 cm$^{-1}$; $^1$H-NMR (CDCl$_3$): δ7.95 (1H,d, J=2 Hz), 7.6 (1H,d, J=9 Hz), 7.4÷7.2 (2H,m), 6.1 (1H,d), 4.2 (1H,m), 2.8 (3H,2), 2.3÷1.1 (10H,m); UV (EtOH): $\lambda_{max}$=227, 250, 276, 305, 323 336 nm. Elementary analysis for C$_{17}$H$_{19}$ClN$_4$ (m.w. 314.82): calcd. C 64.86, H 6.08, N 17.80%; found C 64.86, H 6.21, N 17.91%.

EXAMPLE 22

By reacting 2,3,6,7-tetrachloroquinoxaline with aminoacetaldehyde dimethyl acetal, following a procedure that is similar to that described in example 1, there is obtained 7,8-dichloroimidazo[1,2-a]quinoxalin-4(5H)-one (m.p. >300° C.). By reacting this product with cyclopentylamine according to the method described in example 3, there is obtained 4-cyclopentylamino-7,8-dichloroimidazo[1,2-a] quinoxaline. m.p. (DSC)=139.4° C.(onset); IR (KBr): 3247, 2961, 1589, 1556 cm$^{-1}$; $^1$H-NMR (CDCl$_3$): δ7.8 (2H,m), 7.7 (1H,s), 7.55 (1H,s), 6.2 (1H,d), 4.6 (1H,m), 2.4÷1.3 (8H,m); UV (EtOH): $\lambda_{max}$=235, 274, 292, 304, 330, 345 nm. Elementary analysis for C$_{15}$H$_{14}$Cl$_2$N$_4$ (m.w. 321.21): calcd. C 56.09, H 4.39, N 17.44%; found C 56.13, H 4.41, N 17.52%.

EXAMPLE 23

By reacting 4,7,8-trichloroimidazo[1,2-a]quinoxaline example 22 with cyclohexylamine, following a procedure that is similar to that described in example 3, there is obtained 4-cyclohexylamino-7,8-dichloroimidazo[1,2-a] quinoxalin m.p. (DSC)=162.3° C.(onset); IR (KBr): 3332, 2929, 1587, 1550 cm$^{-1}$; $^1$H-NMR (CDCl$_3$): δ7.8 (2H,m), 7.7 (1H,s), 7.55 (1H,d, J=2 Hz), 6.2 (1H,d), 4.4 (1H,m), 2.3÷1.2 (10H,m); UV (EtOH): $\lambda_{max}$=234, 274, 292, 304, 330, 345 nm. Elementary analysis for C$_{16}$H$_{16}$Cl$_2$N$_4$ (m.w. 344.25): calcd. C 55.82, H 4.98, N 16.28%; found C 55.83, H 5.00, N 16.31%.

EXAMPLE 24

By reacting 2,3,6,7-tetrachloroquinoxaline with propargylamine, following a procedure that is similar to that described in example 2 there is obtained 7,8-dichloro-1-methylimidazo[1,2-a]quinoxalin-4(5H)-one (m.p. >300° C.). By reacting this product with cyclopentylamine according to the method described in example 3, there is obtained 4-cyclopentylamino-7,8-dichloro-1-methylimidazo[1,2-a] quinoxaline. m.p. (DSC)=213.5° C.(onset); IR (KBr): 3411, 2960, 1548, cm$^{-1}$; $^1$H-NMR (CDCl$_3$): δ8.0 (1H,s), 7.75 (1H,s), 7.25 (1H,s), 6.2 (1H,d), 4.6 (1H,m), 2.8 (3H,s), 2.3÷1.3 (8H,m); UV (EtOH): $\lambda_{max}$=233, 279, 308, 337, 341 nm. Elementary analysis for C$_{16}$H$_{16}$Cl$_2$N$_4$ (m.w. 335.23): calcd. C 57.33, H 4.81, N 16.71%; found C 57.41, H 4.82, N 16.68%.

EXAMPLE 25

By reacting 2,3-dichloro-6-fluoroquinoxaline with aminoacetaldehyde dimethyl acetal, following a procedure that is similar to that described in example 1, there is obtained 8-fluoroimidazo[1,2-a]quinoxalin-4(5H)-one (m.p. >300° C.) and, subsequently, 4-chloro-8-fluoroimidazo[1,2-] quinoxaline. By reacting this product with cyclopentyl amine according to the method described in example 3, there is obtained 4-cyclopentylamino-8-dichloroimidazo[1,2-a] quinoxaline. m.p. (DSC)=85.7° C.(onset); IR (KBr): 3255, 2964, 1551 cm$^{-1}$; $^1$H-NMR (CDCl$_3$): δ7.8 (1H,m), 7.7÷7.35 (1H,dd, J$_{HF}$=16 Hz), 7.5 (1H,d, J=2 Hz), 7.6÷7.25 (1H,dd, J$_{HF}$=16 Hz), 7.05 (1H,dd), 6.0 (1H,d), 4.55 (1H,m), 2.35÷1.3 (8H,m); UV (EtOH): $\lambda_{max}$=226, 268, 285, 296, 323, 336 nm. Elementary analysis for $C_{15}H_{15}FN_4$ (m.w. 270.31): calcd. C 66.65, H 5.59, N 20.73%; found C 66.36, H 5.66, N 20.86%.

EXAMPLE 26

By reacting 4-chloro-8-fluoroimidazo[1,2-a] quinoxaline (example 25) with cyclohexylamine, following a procedure that is similar to that described in example 3, there is obtained 4-cyclohexylamino-8-fluoroimidazo[1,2-a] quinoxalin. m.p. (DSC)=157.6° C.(onset); IR (KBr): 3415, 2927, 1556 cm$^{-1}$; $^1$H-NMR (CDCl$_3$): δ7.8 (1H,dd, J=2 Hz), 7.7÷7.35 (1H,dd, $J_{HF}$=16 Hz), 7.55 (1H,d, J=2 Hz), 7.55÷7.25 (1H,dd, $J_{HF}$=16 Hz), 7.05 (1H,dd), 6.0 (1H,d), 4.25 (1H,m), 2.35÷1.2 (10H,m); UV (EtOH): $\lambda_{max}$=226, 239, 285, 297, 323, 337 nm. Elementary analysis for $C_{16}H_{17}FN_4$ (m.w. 284.33): calcd. C 67.59, H 6.03, N 19.71%; found C 67.31, H 6.04, N 19.70%.

EXAMPLE 27

By reacting 2,3-dichloro-6,7-difluoroquinoxaline with aminoacetaldehyde dimethyl acetal, following a procedure that is similar to that described in example 1, there is obtained 7,8-difluoroimidazo[1,2-a]quinoxalin-4(5H)-one (m.p. >300° C.) and, subsequently, 4-chloro-7,8-difluoroimidazo[1,2-]quinoxaline. By reacting this product with cyclopentylamine according to the method described in example 3, there is obtained 4-cyclopentylamino-7,8-dichloroimidazo[1,2-a]quinoxaline. m.p. (DSC)=146.0° C.(onset); IR (KBr): 3263, 2955, 1554 cm$^{-1}$; $^1$H-NMR (CDCl$_3$): δ7.7 (1H,s), 7.65÷7.15 (3H,m), 6.1 (1H,d), 4.6 (1H,m), 2.3÷1.3 (8H,m); UV (EtOH): $\lambda_{max}$=225, 241, 270, 295, 323, 337 nm. Elementary analysis for $C_{15}H_{14}F_2N_4$ (m.w. 288.30): calcd. C 62.49, H 4.89, N 19.43%; found C 62.46, H 5.03, N 19.65%.

EXAMPLE 28

Binding on the adenosine receptors.

The binding on A$_1$ receptors has been carried out according to the method described in Naunyn-Schmied. Arch. Pharmacol. 1987, 336, 204 on preparations of synaptosomial membranes from rat brain by incubating 200 μg of membrane proteins for 1 h at 25° C. with the substance to be tested and 0.3 nM [$^3$H]-DPCPX in 400 μl of 50 mM Tris.HCl pH=7.4. The non-specific binding has been determined with 5 nM R-PIA.

The binding on A$_1$ receptors has been carried out according to the method described in FASEB J. 1989, 3, A1047 on preparations of rat striatal membranes by incubating 200 μg of membrane proteins for 1 h at 25° C. with the substance to be tested, 5 nM [$^3$H]-CGS21680 and 50 nM CPA. The non-specific binding has been determined with 100 nM CPA.

The incubations were blocked by filtration by means of a cell-harvester and, after completion of the separation of the bound from the free, the radioactivity contents were evaluated by liquid scintillation. The concentration-inhibition curves were obtained by assaying the receptor displacement at at least ten different concentrations of the test substance (all the assays were carried out in triplicate). The tested substances were dissolved in dimethyl sulphoxide and diluted in 50 mM Tris.HCl buffer pH=7.4. The IC$_{50}$ values have been determined by non-linear regression curves and transformed into Ki values according to the Cheng-Prusoff equation.

Table I shows the results obtained with the compounds of examples 5, 9, 13, 18, 22 and 25 of the invention.

TABLE I

| | Adenosine receptors affinities: | |
|---|---|---|
| Substance | Ki, A$_1$ (nM) | Ki, A$_1$ (μM) |
| COMPOUND EX. 5 | 54 | |
| COMPOUND EX. 9 | 7, 9 | 2, 5 |
| COMPOUND EX. 13 | — | 2, 6 |
| COMPOUND EX. 18 | 23, 5 | |
| COMPOUND EX. 22 | 26, 5 | |
| COMPOUND EX. 25 | 84 | |

EXAMPLE 29

Forced swim test

The test described by R. D. Porsolt et al. in Arch.Int.Pharmacodyn.Ther. 1977, 229, 327, has been carried out which is widely used as an animal model for the study of the antidepressant activity of new drugs. Male albino CD 1 mice weighing 25–35 g were used.

One hour before immersion in water, the test compound is intraperitoneally (i.p.) administered to the animal; the vehicle is administered to the control animals. The duration of permanence in water is 6'; from the 2$^{nd}$ to the 6$^{th}$ minute the time is measured during which the animal remains motionless. Table II shows the results obtained with the compounds of examples 9, 13, 16, 18 and 21 of the invention, expressed as the percent variation of the immobility time of the treated animals versus the control group. As the reference substance the tricyclic antidepressant drug desipramine was used.

TABLE II

| | Forced swim test | |
|---|---|---|
| Substance | Dose (mg/kg.i.p.) | % variation immobility time vs. C. |
| COMPOUND EX. 9 | 0.001 | −32.8*** |
| COMPOUND EX. 9 | 0.01 | −45.3*** |
| COMPOUND EX. 13 | 0.1 | −23.5* |
| COMPOUND EX. 13 | 1 | −70.7*** |
| COMPDUND EX. 16 | 0.1 | −22.4 |
| COMPOUND EX. 16 | 1 | −51.4*** |
| COMPOUND EX. 18 | 1 | −42.3*** |
| COMPOUND EX. 18 | 10 | −52.8*** |
| COMPOUND EX. 21 | 0.001 | −33.0** |
| COMPOUND EX. 21 | 0.01 | −48.6*** |
| DESIPRAMINE | 7.5 | −10.4** |
| DESIPRAMINE | 30 | −41.4*** |

(*) p < 0.001; () p < 0.01; (*) p < 0.05

EXAMPLE 30

Tail suspension test

The test described by L. Steru, et al. in Psychopharmacology 1985, 85, 367, also widely used as an animal model for the screening of antidepressant activity has been carried out.

Male albino CD 1 mice weighing 25–35 g were used.

Half an hour before the test, the animal is administered the test compound by the i.p. route; the control animals are administered the vehicle. The mouse is suspended from a horizontal bar at about 40 cm from the support plane by means of an adhesive tape applied at the end of the tail and secured to a hook. The immobility time period is registered during 6'.

Table III shows the results obtained with the compound of example 9 of the invention, as the percent change of the immobility time period of the treated animals versus the control group.

As the reference substance the tricyclic antidepressant drug desipramine was used.

TABLE III

| | Tail suspension test | |
|---|---|---|
| Substance | Dose (mg/kg.i.p.) | % variation immobility time vs.C. |
| COMPOUND EX. 9 | 0.001 | −26.7 |
| COMPOUND EX. 9 | 0.01 | −41.1* |
| COMPOUND EX. 9 | 0.1 | −64.3*** |
| DESYPRAMINE | 4 | −21.3 |
| DFSYPRAMINE | 16 | −62.4** |

(*) p < 0.001; () p < 0.01; (*) p < 0.05

What is claimed is:

1. A method of making compounds of the formula (I):

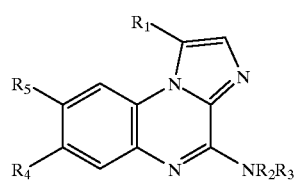

(I)

wherein $R_1$ is hydrogen or methyl;

$R_2$ is hydrogen, straight- or branched- chain ($C_1$–$C_6$) alkyl;

$R_3$ is hydrogen, straight- or branched- chain ($C_1$–$C_8$) alkyl that is optionally substituted with OH, ($C_3$–$C_8$) cycloalkyl; or $R_2$ and $R_3$ together form

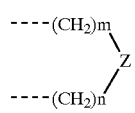

wherein Z is a —$CH_2$— group, a direct bond, or O, $NR_6$, $R_6$ being straight- or branched- chain ($C_1$–$C_6$) alkyl;

m and n are the same and are 2;

$R_4$ and $R_5$ can be the same or different and are hydrogen or halogen chosen from Cl, R, Br; with the proviso that when $R_1$, $R_2$, $R_4$, $R_5$ are hydrogen, $R_3$ cannot be hydrogen, straight or branched-chain ($C_1$–$C_8$) alkyl, ($C_3$–$C_8$) cycloalkyl;

or pharmacologically acceptable salts of said compounds, said method comprising the steps of:

reacting a compound of the formula (II)

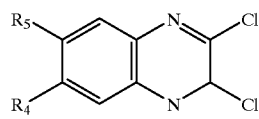

(II)

with amino acetaldehyde dimethyl acetal or with propargyl amine, thereby to obtain, respectively, the compounds of the formulae (III) and (IV)

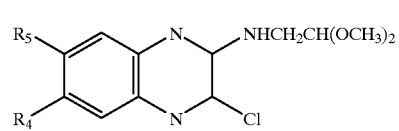

(III)

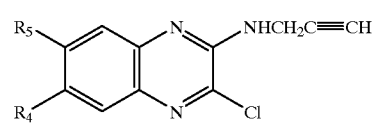

(IV)

cyclicizing said compounds in an acidic medium to generate a compound of formula (V)

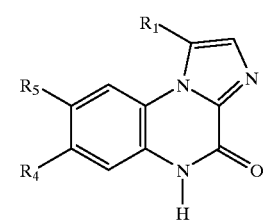

(V)

reacting compound (V) with a chlorinating agent to produce a compound of formula (VI)

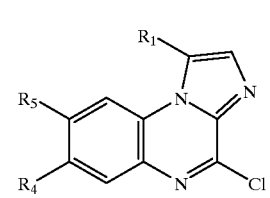

(VI)

and reacting compound (VI) with $HNR_2R_3$, or wherein compound (V) is reacted with a silylating reagent and $HNR_2R_3$ at a temperature between 80 and 180° C.;

or wherein, when R2 and R3 of compound (I) are both hydrogen, compound (VI) is reacted with hydrazine to produce a compound of the formula (VII)

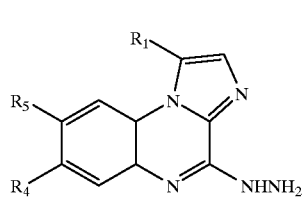

(VII)

said compound (VII) being subsequently hydrogenated.

2. A method of treating depression in a person suffering from the same, comprising administering to such a person a therapeutically effective amount of a compound of the formula (I):

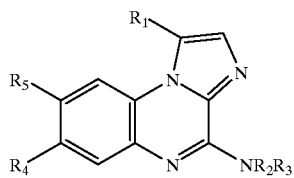
(I)

wherein:

R₁ is hydrogen or methyl;

R₂ is hydrogen, straight- or branched- chain ($C_1$–$C_6$) alkyl;

R₃ is hydrogen, straight- or branched- chain ($C_1$–$C_8$) alkyl that is optionally substituted with OH, ($C_3$–$C_8$) cycloalkyl; or R₂ and R₃ together form

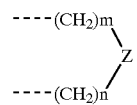

wherein Z is —$CH_2$— group, a direct bond, or O, $NR_6$, $R_6$ being straight- or branched- chain ($C_1$–$C_6$) alkyl;

m and n are the same and are 2;

R₄ and R₅ can be the same or different and are hydrogen or halogen chosen from Cl, F, and Br;

or its pharmaceutically acceptable salts.

3. The method as claimed in claim 2, wherein said effective amount is 0.005–20 mg/kg of body weight per day.

4. The method as claimed in claim 2, wherein said effective amount is 0.5–2 mg/kg of body weight per day.

* * * * *